United States Patent [19]

Buda et al.

[11] 4,073,694
[45] Feb. 14, 1978

[54] MICROBIOLOGICAL ASSAY OF AMINOGLYCOSIDE ANTIBIOTICS

[75] Inventors: Dennis Buda, Baltimore; Rodney L. Broman, Baldwin; John R. Waters, Towson, all of Md.

[73] Assignee: Johnston Laboratories, Inc., Cockeysville, Md.

[21] Appl. No.: 673,359

[22] Filed: Apr. 5, 1976

[51] Int. Cl.$^2$ .............................................. C12K 1/00
[52] U.S. Cl. ......................... 195/103.7; 195/103.5 R; 195/103.5 K
[58] Field of Search ..................... 195/103.7, 103.5 R, 195/103.5 K

[56] References Cited
PUBLICATIONS

Noone et al., Simple, Rapid Method for Assay of Aminoglycoside Antibiotics, Lancet, July 3, 1971, pp. 16–19.
Ibid, Dec. 2, 1972, pp. 1194–1195.

Primary Examiner—Alvin E. Tanenholtz
Assistant Examiner—Robert J. Warden
Attorney, Agent, or Firm—Schuyler, Birch, Swindler, McKie & Beckett

[57] ABSTRACT

A method of measuring the level of an aminoglycoside antibiotic, such as gentamicin, tobramycin or amikacin, in blood serum or plasma comprising incubating an aliquot of blood serum or plasma from a human patient being treated with an aminoglycoside antibiotic in a urea-containing culture medium with a susceptible strain of an adaptive urease producing microorganism corresponding to *Proteus rettgeri* JLI 03, ATCC No. 31168.

9 Claims, 3 Drawing Figures

MICROBIOLOGICAL ASSAY OF AMINOGLYCOSIDE ANTIBIOTICS

BACKGROUND OF THE INVENTION

Aminoglycoside antibiotics, such as gentamicin, tobramycin, amikacin etc. are valuable antimicrobial agents. This is especially true of gentamicin which presently is widely used for treatment of infections due to gram-negative microorganisms. Great care must be taken, however, in administering aminoglycoside antibiotics since the minimum effective dosage level lies close to the threshold of toxicity. Excessive levels of aminoglycoside antibiotics, such as gentamicin in the blood of a human patient can have serious adverse consequences such as deafness and/or kidney damage. Administrations of such antibiotics at levels inadequate to destroy infectious microorganisms, can result in evolution of resistant strains of microorganism. It is therefore critical when using these antibiotics that the level of the antibiotic in the blood of a patient be carefully monitored in order to maintain an effective therapeutic dosage without exceeding the threshold of toxicity.

For assaying the blood level of gentamicin the art has developed procedures based on the fact that gentamicin inhibits the synthesis of the enzyme urease by certain bacteria. Various species of the genus Proteus, for example, are known to synthesize urease in the presence of urea. The urease enzyme attacks, in turn, the urea and destroys it by hydrolyzing it to ammonia and carbon dioxide. The presence of gentamicin in the system, however, inhibits the synthesis of urease by certain Proteus species thereby proportionately reducing the rate at which the urea is hydrolized. The concentration of gentamicin is thus inversely related to the rate of hydrolysis of urea in such a system and may be determined from measurements of the urea hydrolysis. One technique for monitoring the urea hydrolysis rate follows the reduction in the rate of increase in the pH of a culture medium due to the release of ammonia during the hydrolysis; Noone et al., Simple, Rapid Method for Assay of Aminoglycoside Antibiotics, *Lancet* July 3, 1971, pages 16–19. See also ibid. Dec. 2, 1972, pages 1194–1195; ibid. Jan. 6, 1973, pages 49–50, and ibid. Feb. 10, 1973, pages 315–317. It is also known to follow hydrolysis of urea by the enzyme urease by using test media containing urea labeled with radioactive carbon 14 and measuring the evolution of radioactive carbon $^{14}CO_2$. McDonald et al., Urease: A Sensitive and Specific Radiometric Assay, *Enzymologia*, Vol. 42, pages 1–9; DeBersaques, A Micromethod for Urease, *Liquid Scintillation Counting*, Vol. 3, M. A. Crook, ed., Heyden, pages 303–306. A particularly advantageous approach for the assay of gentamacin in blood plasma is detailed in copending U.S. patent application Ser. No. 452,264 now U.S. Pat. No. 3,948,729, owned by the common assignee and incorporated herein by reference. These previously reported bioassays of gentamicin concentration have utilized strains of the species *Proteus mirabilis*.

Microbiological assays of aminoglycoside antibiotic levels are subject to the difficulty that aminoglycoside antibiotics like gentamicin are most commonly administered in conjunction with one or more additional antibiotics. Since the mircroorganisms conventionally utilized for such assays can be, and often are, sensitive to the additional antibiotics present in the patient's blood, the results of the assay may be distorted due to the fact that the additional antibiotic may kill the microorganism; thereby decreasing the synthesis of the enzyme urease and consequently reducing the hydrolysis of ammonia so that the assay erroneously indicates a higher than actual level of aminoglycoside antibiotic in the patient's blood. Representative antibiotics commonly administered in conjunction with aminoglycoside antibiotics such as gentamicin include chloramphenicol, ampicillin, tetracycline, carbenicillin, furadantin, sulfisoxazole, cephalothin and clindamycin. While deactivation of the foregoing antibiotics in order to prevent their interfering with the aminoglycoside antibiotic assay is theoretically possible, it is ordinarily difficult, especially since the testing laboratory may not have been told of the complete antibiotic regimen used on the patient. Accordingly, it is important to have an assay for determining the level of an aminoglycoside antibiotic, such as gentamicin, tobramycin, amikacin, etc., in blood serum or plasma which is not susceptible to interference from other antibiotics commonly administered in conjunction with the aminoglycoside antibiotics.

OBJECTS OF THE INVENTION

Accordingly it is an object of this invention to provide an assay for determining the level of an aminoglycoside antibiotic in blood serum or plasma which is rapid, convenient and accurate.

It is a further object of this invention to provide a method for determining the level of an aminoglycoside antibiotic in blood serum or plasma which is reliable.

It is also an object of this invention to provide a method for determining the level of an aminoglycoside antibiotic in blood serum or plasma which is not subject to interference from other antibiotics commonly administered in conjunction with the aminoglycoside antibiotics.

A further object of this invention is to provide a method for determining the level of an aminoglycoside antibiotic in blood serum or plasma which is not sensitive to the presence of ampicillin, carbenicillin, cephalotin, chloramphenicol, clindamycin, tetracycline, furadantin, or sulfisoxazole.

SUMMARY OF THE INVENTION

These and other objects of the invention are achieved by providing a method of determining the level of an aminoglycoside antibiotic in blood serum or plasma wherein an aliquot of the liquid portion of blood from a patient being treated with an aminoglycoside antibiotic is incubated in a urea containing test medium with a strain of an adaptive urease producing microorganism corresponding to *Proteus rettgeri* JLI 03, ATCC No. 31168.

DETAILED DESCRIPTION OF THE PREFERRED EMBODIMENT

Figure 1:
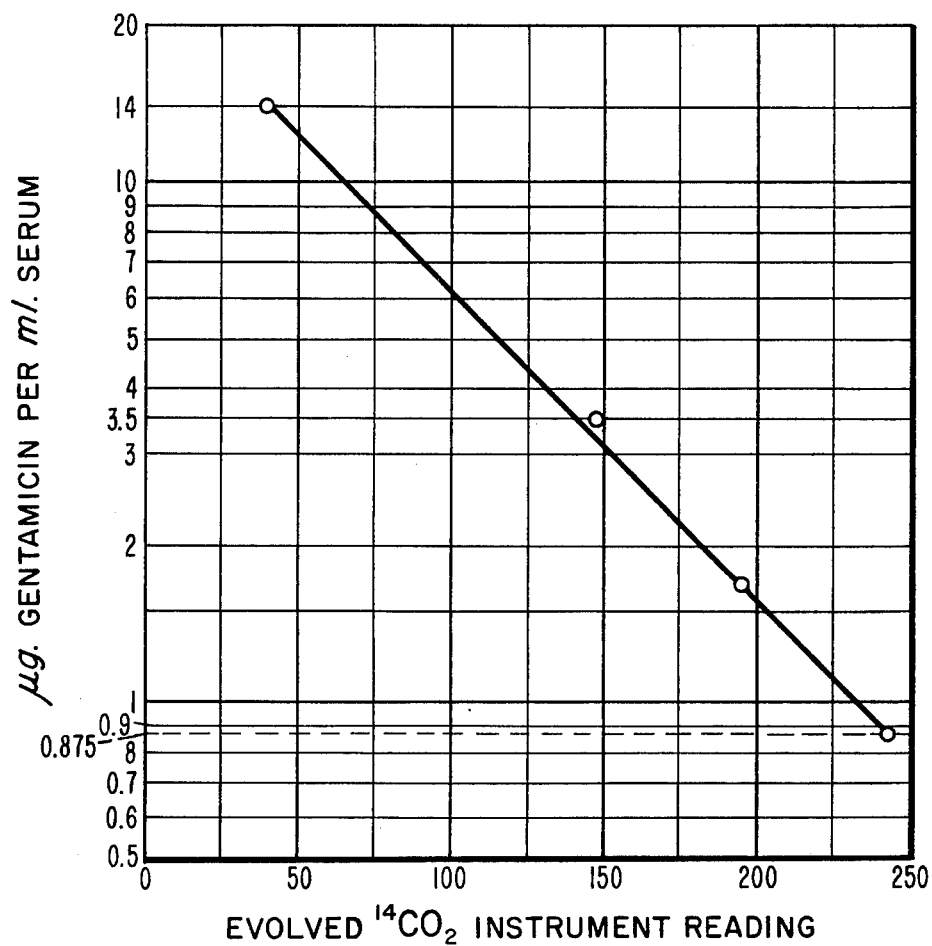
FIG. 1 is a graph of the results from a test assay of gentamicin performed according to the method of the present invention.

While the invention is useful in the assay of aminoglycoside antibiotics generally such as tobramycin and amikacin, it will be described in detail hereinafter with reference to the assay of gentamicin.

In the assay of the invention an appropriate amount of blood serum or plasma from a patient being treated with gentamicin is added to a sterile test medium in an appropriate container. The amount of blood serum required for each test depends on other parameters of the test but generally will lie within the range between about 0.1 ml and about 0.5 ml. In view of the difficulties in extracting large amounts of serum from a patient, it is desirable to keep the amount of serum required toward the low end of the range. Ordinarily about 0.2 ml of blood serum is adequate for testing.

A preferred test media comprises about 0.8% nutrient broth and optionally about 0.2% glucose. The glucose serves as an energy source for the adaptive urease producing microorganism. The initial pH of the test medium should lie between about 7.0 and about 8.5. In the most preferred embodiment of the assay of the invention the initial pH of the test medium is about 7.4. It is preferred that the medium be unbuffered as buffer salts may interfere with the urease synthesis inhibiting activity of the gentamicin. Since calcium and magnesium ions may, under some circumstances, interfere with urease synthesis inhibiting activity of gentamicin, it is recommended that the test medium be free of such ions. During an incubation, the pH of the solution increases indicating that the solution is becoming more basic. Since $CO_2$ is soluable in base, strong acid is added to the vials at the end of the incubation period to release the $CO_2$ from solution and to terminate any further production of $CO_2$.

If, as ordinarily will be the case, the test sample results are to be evaluated by comparing them with simultaneously processed control samples containing known amounts of gentamicin, then it may be necessary to add an amount of distilled water to the test sample to compensate for the dilution of the control samples resulting from the addition of standard solutions of gentamicin.

A viable inoculum of an adaptive urease producing microorganism corresponding to *Proteus rettgeri* JLI 03, is then added to the serum containing test medium. This microorganism has been deposited with the American Type Culture Collection 12301 Parklawn Dr. Rockville, Md. 20852 and has been assigned the reference number ATCC No. 31168. This microorganism is especially adapted for use as the adaptive urease producing microorganism in the assay of the invention because it is resistant to the major antibiotics commonly administered in conjunction with the aminoglycoside antibiotics such as gentamicin. Specific resistances of the *Proteus rettgeri* JLI 03 microorganism include resistance to ampicillin, carbenicillin, cephalothin, chloramphenicol, clindamycin, tetracycline, furadantin, kanamycin, and sulfisoxazole. Use of the *Proteus rettgeri* JLI 03 microorganism as the adaptive urease producing microorganism in the assay of the invention thus prevents distortion of the test results which otherwise could occur as a result of sensitivity of an adaptive urease producing microorganism to the incidental presence of one or more of the foregoing antibiotics.

The number of microorganisms required in the test inoculum may vary from about $10^6$ microorganisms to about $10^8$ microorganisms. Most preferably the inoculum will comprise from about $5 \times 10^6$ to about $5 \times 10^7$ microorganisms. It is preferred to avoid the use of lyophilized (freeze-dried) microorganism inocula because of the presence of excessive numbers of dead and/or broken cells in such samples. Proper size of the adaptive urease producing microorganism inoculum is necessary in order to insure synthesis of adequate amounts of urease in order to hydrolyze detectable amounts of urea while avoiding hydrolysis of such excessive amounts of urea that the hydrolysis products exceed readily manageable levels.

Immediately after addition of the adaptive urease producing microorganism inoculum, the test medium is shaken to insure thorough mixing and thereafter incubated for a period of time at a temperature between 35° and about 39° C. The preferred incubation temperature is about 37° C. Variations of temperature from the 37° preferred incubation temperature or of the initial pH from optimum values between 7.6 and 7.2 may decrease the rate of urease hydrolysis of urea thereby requiring longer incubation periods.

After completion of the desired incubation period, the reaction is quenched to terminate further activity. Termination may be effected in various ways such as by heating or by addition of a terminator substance. A preferred reaction terminator is sulfuric acid. It is desirable to add sufficient acid to adjust the pH of the test medium to a pH not greater than about 2. Since addition of acid will release carbon dioxide produced by the hydrolysis of urea from the solution which may cause some foaming of the test medium, it may be advisable to add a small amount of an anti-foamant with the reaction terminator. One particularly suitable anti-foaming agent is Dow Chemical anti-foamant FG-10 manufactured by Dow Chemical Co., Midland, Mich. The incubated assay is then ready to be read by measuring the amount of hydrolysis of urea which has taken place.

Various procedures have been devised for measuring the extent of urea hydrolysis. The most preferred procedure according to the present invention is to perform the assay using radioactive $^{14}C$-labeled urea in a gas-tight container and after using an acid reaction terminator, measuring the amount of radioactive $^{14}CO_2$ released into the gases above the test medium in the reaction vessel. For example the assay is advantageously carried out in a vial capped with a self-sealing rubber septum. Measurement of the radioactive $^{14}CO_2$ in the atmosphere of the vial may be effected by use of apparatus such as disclosed in Waters, U.S. Pat. No. 3,676,679 incorporated herein by reference, which apparatus is manufactured and marketed by Johnston Laboratories Inc., Cockeysville, Md.

The degree of radioactive labeling of the urea in a given test solution is expressed in terms of a specific activity coefficient which is derived by dividing the total radioactivity in microcuries by the total urea content in micromoles. Typically, the specific activity will be less than 0.001 microcuries per micromole. Since isotopically labeled compounds are expensive it is desirable to use minimum operable amounts of radioactive materials. The assay of the invention utilizing the *Proteus rettgeri* JLI 03 microorganism is so sensitive that acceptable test results may be obtained utilizing test media having specific activities as low as 0.0001 microcuries per micromole. Preferably the specific activity is maintained below 0.001 microcuries per micromole.

Since the hydrolysis of urea depends on the quantity of urease in the test medium which in turn depends upon the number of microorganisms in the inoculum and since the concentration of microorganism in the inoculation medium changes geometrically over the course of time as a result of the natural growth process of the culture, it is advisable to compare the result of the test sample against simultaneously processed control samples containing known amounts of gentamicin processed in an identical manner to the test sample. Control samples may be made up by adding like quantities of pooled normal human serum and like microorganism inocula to like quantities of test medium containing known amounts of aminoglycoside antibiotic, and mixing, incubating, terminating and reading the control samples in the same manner as the test sample. It has been found useful to utilize three control samples containing low, intermediate and high concentrations of gentamicin respectively. For example, control samples containing amounts of gentamicin corresponding to blood serum levels of 1 microgram per ml, 4 micrograms per ml, and 16 micrograms per ml have been found adequate comparision standards in ordinary circumstances. The control serum is pooled from at least three individual donors. The various gentamicin standards can be made up by appropriate dilution of a single stock solution.

The results of the assay are analyzed by plotting the results of the control samples containing known concentrations of gentamicin on semi-logarithmic paper to obtain a standard curve, the ordinate being the concentration of gentamicin in micrograms per ml and the abcissa being the measured value for the evolved carbon dioxide. The concentration of gentamicin in the test sample is then determined by comparing the measured value for carbon dioxide released from the test sample to the standard curve.

The *Proteus rettgeri* JLI 03 microorganism can be maintained by subculturing weekly in a medium comprising about 0.8% nutrient broth, 1% yeast extract, and 0.2% glucose buffered to a pH of approximately 7.4. The subculture is grown overnight at 37° C for 18 and stored at 4° C for a week. Daily transfers to chocolate agar slants are made from the refrigerated broth cultures. These chocolate agar slants are incubated at 37° C for 18 hours and the microorganisms washed from the agar surface with about 5 ml of sterile media mentioned above. This culture suspension is used to inoculate the test vials.

The invention will be further described with reference to the following examples which are illustrative only and are not to be construed as limiting the scope of the invention.

EXAMPLE 1

Four sterile, 20 cc bottles are marked respectively Unknown, Control I, Control II and Control III. Into each bottle is added 2 ml of a test medium comprising about 0.8% nutrient broth, about 0.2% filter sterilized glucose, and about 4% radioactive $^{14}$C-labeled urea having a radioactivity of approximately 0.5 microcuries per ml. The specific activity of the $^{14}$C-labeled urea is thus about 0.00075 microcuries per micromole. Into the bottle marked Unknown is added 0.2 ml of blood serum from a patient being treated with gentamicin. Into each bottle marked Control is added 0.2 ml of pooled normal human serum from three individual donors. Into the bottle marked Unknown is added 0.2 ml of distilled water, and into the bottle marked Control I is added 0.2 ml 0.875 microgram gentamicin per ml stock solution; into the bottle marked Control II is added 0.2 ml of a 3.5 micrograms gentamicin per ml solution, and into the bottle marked Control III is added 0.2 ml of a 14 micrograms gentamicin per ml stock solution. At this point all of the bottles are capped with rubber septa and metal caps. Three tenths ml of a culture of *Proteus rettgeri* JLI 03, ATCC No. 31168 containing between $1 \times 10^8$ and $1 \times 10^9$ microorganisms per ml is injected into each bottle after which the bottles are shaken to mix the contents and then incubated for 1 hour in a 37° C water bath. At the end of 1 hour incubation, 0.5 ml of a reaction stopper made by adding 6.2 ml of concentrated sulfuric acid to 93.8 ml of water and 1 ml of Dow Chemical FG-10 anti-foamant is added to each bottle. The radioactive $^{14}CO_2$ in the gas space of each bottle is then measured on a Bactec Model 301 microbiological activity detector with expanded scale capability, and the results of the control standards are plotted on semi-logarithmic graph paper. A graph of the results is shown in FIG. 1. The bottle marked Control I gave an instrument reading of 243; that marked Control II gave a reading of 145; that marked Control III gave a reading of 38; and that marked Unknown a reading of 195. Comparison of the $^{14}CO_2$ measurement from the test sample to the standard curve plotted from the $^{14}CO_2$ measurements of the control samples reveals the concentration of gentamicin in the blood serum of the patent to be 1.7 micrograms per ml.

EXAMPLES 2-7

These examples demonstrate the resistance of *Proteus rettgeri* JLI 03 to other antibiotics most frequently administered in conjunction with gentamicin. The procedure of Example 1 is repeated on samples of pooled human serum which are identical in all respects except that in Examples 3 through 7 additional antibiotics are present in the serum samples as indicated in Table I:

TABLE I

| Example | Antibiotic (µg/ml) | Evolved $^{14}CO_2$ Instrument Reading |
|---------|--------------------|----------------------------------------|
| 2 | none | 360 |
| 3 | Carbenicillin (200) | 355 |
| 4 | Ampicillin (200) | 360 |
| 5 | Cloramphenicol (25) | 365 |
| 6 | Cephalothin (200) | 355 |
| 7 | Clindamycin (150) | 355 |

In each case the amount of $^{14}CO_2$ released in the presence of the additional antibiotics in Examples 3–7 was substantially unaffected in comparision to control Example 2 containing no additional antibiotic.

EXAMPLES 8-13

The procedure of Examples 2 through 7 was repeated except that the microorganism used as the adaptive urease producing organism was *Proteus mirabilis* TM 101, ATCC No. 31008. This organism is sensitive to all of the additional antibiotics tested except clindamycin. The results are shown in Table II:

TABLE II

| Example | Additional Antibiotic (µg/ml) | Evolved $^{14}CO_2$ Instrument Reading |
|---------|-------------------------------|----------------------------------------|
| 8 | none | 507 |
| 9 | Carbenicillin (200) | 495 |
| 10 | Ampicillin (200) | 458 |
| 11 | Chloramphenicol (25) | 480 |
| 12 | Cephalothin (200) | 451 |
| 13 | Clindamycin (150) | 506 |

In each case where the orgainsm is sensitive to the additional antibiotic, the amount of $^{14}CO_2$ released is reduced compared to control Example 8 containing no additional antibiotic. These examples demonstrate the effect such antibiotics have on *Proteus mirabilis* TM 101 urease synthesis which in a gentamicin assay can lead to erroneously high values for gentamicin in the test serum.

EXAMPLES 14–19

The procedure of Examples 2–7 was again repeated except that a strain of *Proteus rettgeri* identified as *Proteus rettgeri* JLI 05 was utilized as the adaptive urease producing microorganism. This organism is of the same genus and species as that used in Examples 2–7, however it is sensitive to the additional antibiotics tested with the exception of cephalothin. The results are shown in Table III.

TABLE III

| Example | Additional Antibiotic (µg/ml) | Evolved $^{14}CO_2$ Instrument Reading |
|---|---|---|
| 14 | none | 144 |
| 15 | Carbenicillin (200) | 136 |
| 16 | Ampicillin (200) | 132 |
| 17 | Chloramphenicol (25) | 126 |
| 18 | Cephalothin (200) | 142 |
| 19 | Clindamycin (150) | 127 |

As can be seen from Examples 14–19, when the test organism is sensitive to the additional antibiotic, the amount of $^{14}CO_2$ released is reduced compared to control Example 14 which contains no additional antibiotic. As noted previously, in a gentamicin assay this can lead to erroneously high values for gentamicin in the test serum.

EXAMPLE 20

The procedure used to produce the three control samples of Example 1 is repeated except that amikacin is used as the aminoglycoside antibiotic instead of gentamicin. The results are shown in Table IV.

TABLE IV

| Amikacin (µg/ml) | Evolved $^{14}CO_2$ Instrument Reading |
|---|---|
| 0.87 | 150 |
| 3.5 | 114 |
| 14 | 35 |

Figure 2:
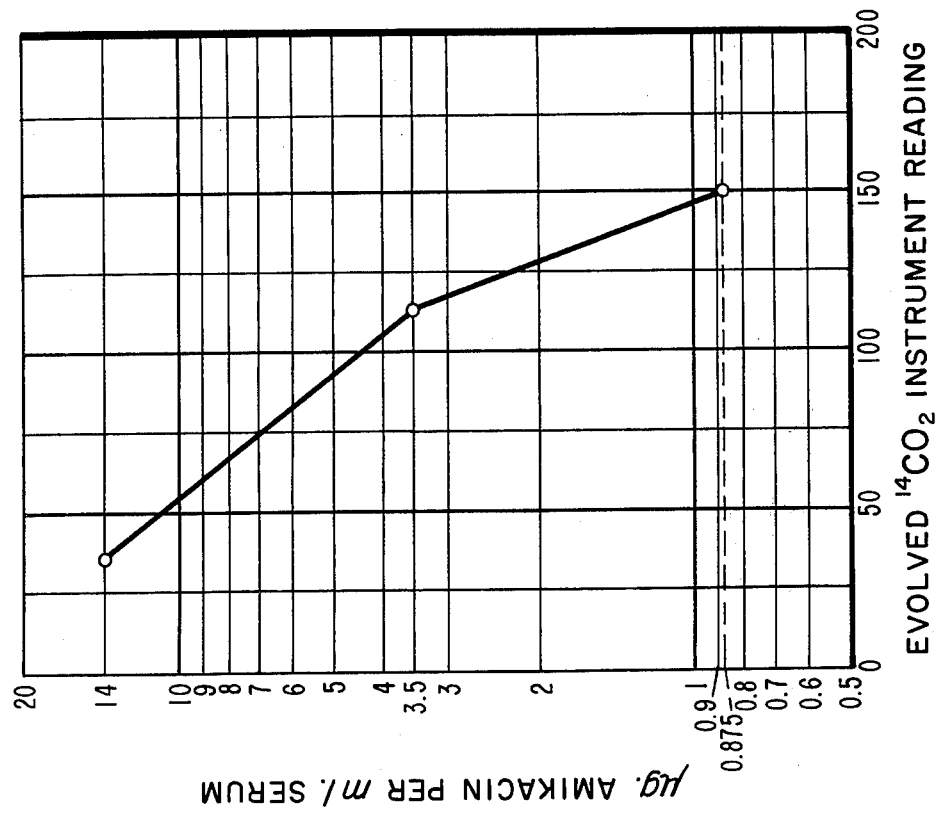
FIG. 2 is a graph of a standard curve for the assay of amikacin.

When plotted, this data produces a standard curve for the assay of amikacin as shown in FIG. 2.

EXAMPLE 21

The procedure used to produce the three control samples of Example 1 is again repeated except that tobramycin is used as the aminoglycoside antibiotic instead of gentamicin. The results are listed in Table V.

TABLE V

| Tobramycin (µg/ml) | Evolved $^{14}CO_2$ Instrument Reading |
|---|---|
| 0.87 | 186 |
| 3.5 | 123 |
| 14 | 35 |

Figure 3:
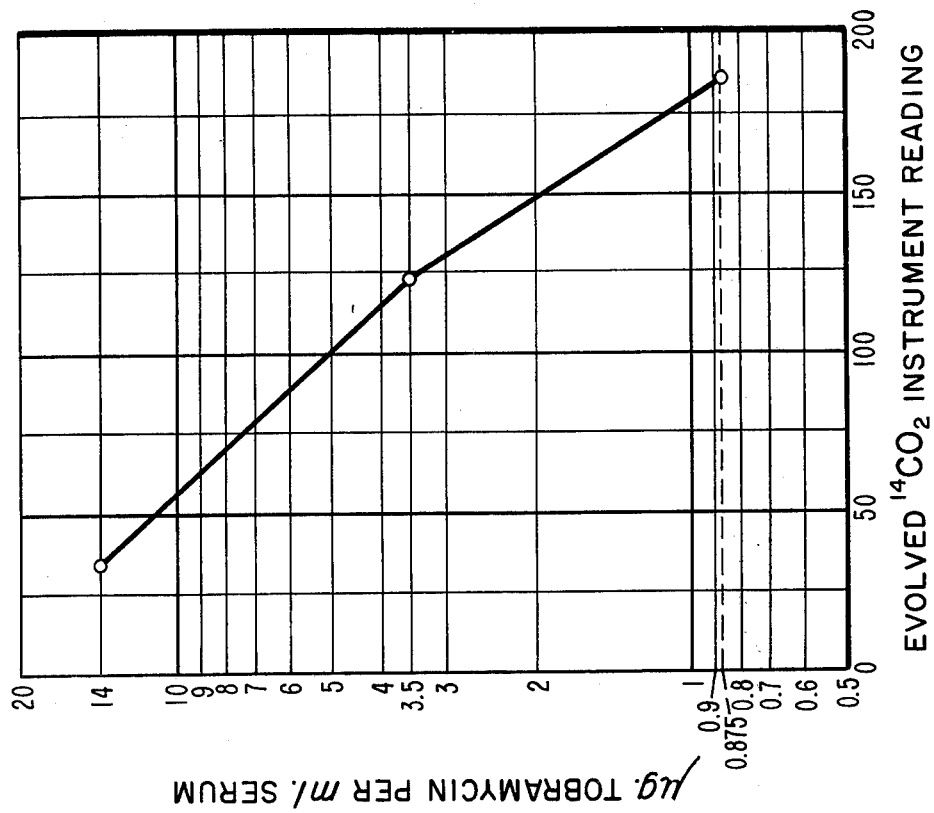
FIG. 3 is a graph of a standard curve for the assay of tobramycin.

When plotted, this data produces a standard curve for the assay of tobramycin as shown in FIG. 3.

Since modifications of the invention may occur to others skilled in the art, the scope of the invention is to be limited solely by the scope of the appended claims.

We claim:

1. In a method of determining the concentration of an aminoglycoside antibiotic in blood wherein an aliquot of the liquid portion of blood from a patient being treated with said aminoglycoside antibiotic is incubated in a urea containing test medium with a susceptible strain of an adaptive urease producing microorganism, the improvement comprising using a microorganism having the characteristics of *Proteus rettgeri* JLI 03, ATCC No. 31168 as the adaptive urease producing microorganism.

2. A method as recited in claim 1 wherein said aminoglycoside antibiotic is gentamicin.

3. A method as recited in claim 1 wherein said aminoglycoside antibiotic is amikacin.

4. A method as recited in claim 1 wherein said aminoglycoside antibiotic is tobramycin.

5. A method as recited in claim 1 wherein said test medium comprises $^{14}C$-labeled urea and said method further comprises determining the amount of $^{14}CO_2$ produced during the incubation.

6. A method as recited in claim 5 wherein the specific activity of said $^{14}C$-labeled urea is less than 0.001 microcuries per micromole.

7. A method as recited in claim 5 wherein the test medium is acidified after incubation to release $^{14}CO_2$ from the test medium and the evolved $^{14}CO_2$ is measured in the vapor phase.

8. A method as recited in claim 5 wherein the amount of $^{14}CO_2$ produced during the incubation is compared with that produced from control media containing an aliquot of pooled normal liquid from human blood and known concentrations of aminoglycoside antibiotic processed in the same manner.

9. A method as recited in claim 6 wherein the initial pH of the test medium lies between about 7.0 and about 8.5, the initial inoculation of microorganism into the test medium comprises from about $10^6$ to about $10^8$ microorganisms and the incubation is carried out at a temperature lying in the range from about 35° C to about 39° C for a period of time less than about 2 hours.

* * * * *